US010973347B2

(12) United States Patent
Bissen et al.

(10) Patent No.: US 10,973,347 B2
(45) Date of Patent: Apr. 13, 2021

(54) SMART CARAFE HAVING LIGHT EMITTING CLOSURE

(71) Applicant: RIPRUP Company S.A., St. Peter Port (GG)

(72) Inventors: Monique Bissen, Pforzheim (DE); Josef Schucker, Ronco Sopra Ascona (CH)

(73) Assignee: RIPRUP Company S.A., Guernsey (GY)

( * ) Notice: Subject to any disclaimer, the term of this patent is extended or adjusted under 35 U.S.C. 154(b) by 186 days.

(21) Appl. No.: 16/043,528

(22) Filed: Jul. 24, 2018

(65) Prior Publication Data

US 2019/0021527 A1 Jan. 24, 2019

(30) Foreign Application Priority Data

Jul. 24, 2017 (EP) ...................................... 17182881
Jul. 17, 2018 (EP) ...................................... 18183998

(51) Int. Cl.
*A47G 19/12* (2006.01)
*B65D 51/24* (2006.01)
(Continued)

(52) U.S. Cl.
CPC ......... *A47G 19/12* (2013.01); *A47G 19/2227* (2013.01); *A47G 19/2272* (2013.01);
(Continued)

(58) Field of Classification Search
CPC .......... A47G 2200/08; A47G 2200/085; A47G 19/12; A47G 19/127; A47G 2019/122;
(Continued)

(56) References Cited

U.S. PATENT DOCUMENTS 299,676 A * 6/1884 Poland .................. B65D 39/12
215/361
4,184,603 A * 1/1980 Hamilton, Sr. ..... A47G 19/2272
220/254.5
(Continued)

FOREIGN PATENT DOCUMENTS

WO    WO-0128881 A1 *  4/2001  ............. B65D 39/12
WO    WO-2010118519 A1 * 10/2010  ............... G09F 9/33
(Continued)

OTHER PUBLICATIONS

EPO: "European Search Report"; Application No. EP18183998; dated Nov. 22, 2018.

*Primary Examiner* — David L Singer
(74) *Attorney, Agent, or Firm* — Bryan W. Bockhop; Bockhop IP Law, LLC

(57) ABSTRACT

A beverage vessel having an upper opening and a closure element with a locking mechanism and an actuation element, a light distribution element arranged at the closure element, and a light emitter positioned such that the light emitted by the light emitter passes at least a part of the volume of the beverage container before entering the light distribution element. The light emitter may display information relating to the beverage including temperature and fill level. The beverage vessel may be utilized in a method of monitoring a beverage consumption and a consumption of minerals.

14 Claims, 5 Drawing Sheets

(51) Int. Cl.
*B65D 55/02* (2006.01)
*B65D 39/12* (2006.01)
*A47G 23/16* (2006.01)
*A47G 19/22* (2006.01)
*G16H 20/30* (2018.01)
*G16H 20/60* (2018.01)
*G08B 5/36* (2006.01)
*G01F 23/00* (2006.01)
*H04B 1/02* (2006.01)
*G08B 7/00* (2006.01)
*G01F 23/26* (2006.01)

(52) U.S. Cl.
CPC .............. *A47G 23/16* (2013.01); *B65D 39/12* (2013.01); *B65D 51/245* (2013.01); *B65D 55/02* (2013.01); *G16H 20/30* (2018.01); *G16H 20/60* (2018.01); *A47G 2019/225* (2013.01); *A47G 2019/2238* (2013.01); *A47G 2019/2244* (2013.01); *A47G 2200/066* (2013.01); *A47G 2200/08* (2013.01); *A47G 2200/085* (2013.01); *A47G 2200/166* (2013.01); *A47G 2200/183* (2013.01); *A47G 2200/205* (2013.01); *A47G 2200/226* (2013.01); *G01F 23/0015* (2013.01); *G01F 23/0076* (2013.01); *G01F 23/263* (2013.01); *G08B 5/36* (2013.01); *G08B 7/00* (2013.01); *H04B 1/02* (2013.01)

(58) Field of Classification Search
CPC ............ A47G 2019/2238; A47G 23/16; A47G 19/2272; A47J 41/0016; A47J 41/0022; B65D 51/245; B65D 39/12; B65D 2543/00046; B65D 55/02; G08B 5/36; G08B 5/38
USPC ........................................................ D7/900
See application file for complete search history.

(56) References Cited

U.S. PATENT DOCUMENTS

| | | | |
|---|---|---|---|
| 9,163,826 B1* | 10/2015 | Citrin | A47G 19/2227 |
| 10,433,666 B1* | 10/2019 | Jovanov | A61J 7/0076 |
| 2001/0050289 A1* | 12/2001 | Cordes | G09F 27/00 |
| | | | 222/39 |
| 2006/0139928 A1* | 6/2006 | Griffiths | B65D 51/248 |
| | | | 362/276 |
| 2006/0261233 A1* | 11/2006 | Williams | A61J 9/00 |
| | | | 248/311.2 |
| 2008/0022767 A1* | 1/2008 | Ramus | A47J 31/44 |
| | | | 73/304 C |
| 2008/0112459 A1* | 5/2008 | Salkeld | A47G 19/2272 |
| | | | 374/141 |
| 2011/0050431 A1* | 3/2011 | Hood | G01N 33/14 |
| | | | 340/603 |
| 2015/0307245 A1* | 10/2015 | Puccini | B65D 41/02 |
| | | | 215/228 |
| 2016/0058225 A1* | 3/2016 | Wells | F21V 23/04 |
| | | | 362/101 |
| 2016/0159632 A1* | 6/2016 | Wheatley | G16H 20/13 |
| | | | 222/1 |
| 2016/0194125 A1* | 7/2016 | Bentkovski | B65D 51/2807 |
| | | | 206/221 |
| 2016/0286993 A1* | 10/2016 | Pau | A47G 19/2288 |
| 2017/0158388 A1* | 6/2017 | Bentkovski | A61J 7/04 |
| 2017/0340147 A1* | 11/2017 | Hambrock | G01F 23/263 |
| 2018/0305091 A1* | 10/2018 | Krafft | A47G 19/2227 |

FOREIGN PATENT DOCUMENTS

| | | | |
|---|---|---|---|
| WO | WO-2015175969 A1 * | 11/2015 | ............ G01J 3/0256 |
| WO | WO-2016042562 A2 * | 3/2016 | ............ G06Q 10/087 |
| WO | 2016/090235 A1 | 6/2016 | |
| WO | WO 2016/090235 A1 | 6/2016 | |
| WO | 2016/145027 A1 | 9/2016 | |
| WO | 2016155538 A1 | 10/2016 | |
| WO | WO 2016/155538 A1 | 10/2016 | |

* cited by examiner

SMART CARAFE HAVING LIGHT EMITTING CLOSURE

CROSS-REFERENCE TO RELATED APPLICATION(S)

This application claims the benefit of European Patent Application Nos. EP17182881.7, filed Jul. 24, 2017, and EP18183998.6 filed Jul. 17, 2018 the entirety of each of which is hereby incorporated herein by reference.

BACKGROUND OF THE INVENTION

1. Field of the Invention

The present invention relates to a smart beverage vessel or a smart carafe for monitoring the water consumption of a user of the beverage vessel and for ensuring that a beverage of reasonable quality is provided to the user. Further, germ formation can be avoided.

2. Description of the Related Art

Depending on the physical activity of the user a user has to drink a certain amount of water comprising certain types and amounts of minerals.

Generally, water is consumed by humans increasingly from bottles, since tap water is not considered to be tasty or is more or less polluted. These circumstances cause negative effects. A big share of the bottles is plastic bottles. Such plastic bottles emit substances hazardous to health. Further, the environment is polluted by plastic bottles.

In the heat of the summer the plastic bottle may get very hot, even during delivering the bottle to a customer. Thereby, even more substances hazardous to health can be emitted from the plastic to the water. Plastic is a nutrient medium for bacteria multiplying in the heat in the bottle. Accordingly, the quality of water in the bottle is unknown.

Drinking vessels of the prior art do not monitor quality of the beverage stored in the drinking vessel.

Carafes are used when a group of persons wishes to drink the same beverage, such as during breakfast, lunch, dinning or during a meeting.

Carafes of the prior art face the problem that portions of a closure element over which water flows have to be touched by hand. This is not desired under hygienic considerations.

Further, closure elements of carafes of the prior art comprise plastics that may get into contact with the beverage. This is also not desired under hygienic considerations.

Further, the quality of the water in the carafe has to be monitored and the user has to be informed, if the quality of the water in the beverage vessel is too low.

W0 2016/090235 A1 relates to a portable vessel, wherein additives located in containers can be added to water in the vessel. This system has the disadvantage that the quality of the water cannot be monitored and that it is intricate for the user to carry a comparably bulky beverage vessel with a plurality of containers throughout their working days and leisure days.

WO 2016/155538 A1 discloses a vessel that can monitor drinking events.

It is an object of the present invention to provide an improved beverage vessel that solves the problems of the prior art.

SUMMARY OF THE INVENTION

A beverage vessel according to a first aspect of the present invention comprises a beverage container, a closure element, a light distributor element and a light emitter. In the beverage container beverage may be stored. The beverage container has an upper opening through which beverage may be poured in and poured out of the beverage container and a wall extending from the opening at the top to the bottom of the beverage container. The beverage container may be rotationally symmetric along the vertical axis of the beverage container. The closure element is adapted to be releasably positioned in the upper opening of the beverage container. The light distribution element is arranged at the closure element. The light emitter is positioned such that the light emitted by the light emitter passes at least a part of the volume of the beverage container before entering the light distribution element. The light distribution element is adapted to distribute the light entering from the light emitter in the periphery of the beverage vessel.

The inventive configuration allows combining design aspects and functional aspects. The light emitter may be positioned at a location close to a controller and an accumulator. The light distribution element may be positioned remote and spaced apart from the light emitter and integrated into the design of the beverage vessel, such as a smart carafe, smart bottle or the like. The light emitter may display at least one information relating to the beverage in the beverage container by an optical signal. The light distribution element distributes the light emitted by the light emitter in the periphery of the beverage vessel. Thereby, the user of the beverage vessel or service staff can recognize that action is required, such as refilling the beverage vessel, replacing the beverage in the beverage vessel.

The light distributor element may have opaque optical properties, scattering optical properties and/or diffracting optical properties for appropriate light distribution around the beverage vessel, such that the light and the information about the beverage may be recognized by the user and service staff in the periphery of the beverage vessel.

In one embodiment, the light distribution element may be positioned atop of the closure element.

The closure element may comprise a light guide, a hollow portion or the like for passing light emitted by the light emitter to the light distribution element after it has passed through the beverage container and/or the beverage in the beverage container.

The light emitter may transmit light in a plurality of different colors. The light emitter may transmit continuous light, flashing light or light periodically changing color, e.g. for transmitting information.

In one embodiment the light emitter is positioned at the bottom of the beverage container. The light may pass through the beverage.

The beverage vessel according to a second aspect may comprise a closure element comprising a locking mechanism. The locking mechanism comprises at least three locking arms extending in radial direction of the beverage container to the beverage container. At least one arm of the locking element comprises an elastic portion being elastic in the radial direction of the beverage container.

In one embodiment, the locking element may only be elastic in the radial direction. However, the locking element may also be elastic in another direction.

The beverage container may comprise at least one concave portion in the wall, wherein the concave portion extends in the radial direction of the beverage container. The concave portion extends in the radial a direction from the inner to the outer of the beverage container. The concave portion forms a recess directed to the middle axis of the beverage container. The arms releasably engage the concave portion in the wall for releasably locking the closure element to the beverage container.

The closure element can be pushed by a user into the beverage container through the upper opening. The locking arms are retracted by the outward tapper of the beverage container next to the opening. In other words, around the opening a portion inclined in the radial direction providing the outward tapper is provided for conveniently pouring beverage out of the beverage container. Below the outward tapper the concave portion is provided that extends radially from the inner of the beverage container to the outer of the beverage container.

As soon as the locking arms are pushed downward in the direction of the concave portion, the locking arms extend radially and engage in the concave portion, such that the locking mechanism locks the closure element to the beverage container that closure element cannot be moved downward or upward.

In one embodiment the locking mechanism can only be moved outward (upward), if the mechanical resistance caused by the locking arms engaging into the concave portion is surmounted. The mechanical resistance is caused by the locking arms that are pushed radially inward to the elastic portion of the locking arms. As soon as the locking arms have been pressed inwardly by the boarder or edge of the concave portion, the locking mechanism and closure element can be moved upwardly and the locking arms are released as soon as they are in contact with the inclined portion of the upper tapper at the opening.

The locking arms engage into the concave portion extending radially outward in the container in a snap/fit manner. Operation of such snap/fit mechanism is known by the person skilled the art.

In one embodiment the beverage container may comprise a plurality of concave portions, such as one concave portion for each locking arm.

In a preferred embodiment the concave portion extends in the circumferential direction along the wall of the beverage container. In the cross section direction the concave portion of the container extends radially outward. The concave portion may extend around the beverage container.

The locking arm may comprise at the radially outer tip a contact element elastically accommodated by the locking arm. The contact element may comprises a round shape at the radially outer portion. The round shape may include a partial sphere, a sphere, a partial ellipsoid, an ellipsoid or the like.

The locking arm may comprise an opening extending in the radially direction. The contact element may move into the opening of the locking arm, if a force is exerted on the contact element, such as by the beverage container and particularly from the tapered outlet portion and the concave portion. In the opening of the locking arm an elastic element can be provided, such as a spring that contacts the contact element and the inner end of the opening in the locking arm.

In one embodiment the contact element may comprise at its radially outer portion a partial spherical shape. The contact element may comprise in its radially inner portion a rod shaped portion that is surrounded by the walls of the opening, wherein the rod shaped portion of the contact element is accommodated movably in the radial direction of the locking arm within the opening. The rod shaped portion may comprise a circular or rectangular cross-section.

The closure element may comprise a grip element extending from the grip element in vertical direction of the beverage vessel and/or perpendicular to the locking arms. The grip element extends upward in the vertical direction of the beverage vessel and does not enter the beverage vessel, when the locking arms are engaged in the concave portion. The user can hold the closure element at the grip element and does not have to touch any surface of the closure element or the beverage container that is also contacted by the beverage in the beverage container. Thereby, a beverage vessel and a closure element can be provided that can fulfill ambitious hygienic standards.

The closure element may comprise an actuation element movably mounted on the closure element. The actuation element can be moved in a first position, in which the locking arms are movable in the horizontal direction and in a second position, in which the locking arms are not movable. The actuation element may be movable in the vertical direction. The actuation element can be the grip element or part of the grip element.

In one embodiment the light distribution element is arranged at the actuation element and/or grip element. Preferably, the light distribution element is arranged at the top of the actuation element and/or grip element.

The light distribution element may be a partial sphere positioned at the top of the actuation element.

The beverage vessel may comprise a lid positioned under the grip element and above the locking mechanism. The lid is movable with respect to the locking mechanism. Since the lid is mounted on the locking mechanism, the user does not touch the lid when pressing the closure element into the upper opening of the beverage container. Thereby, high hygienic standards can be provided.

In one embodiment the lid is mounted to the locking mechanism.

In one embodiment the lid is mounted to the locking mechanism by at least one rod extending through an opening in the locking arms. The rod may extend perpendicular to the lid, i.e. in the vertical direction. The opening in the locking arm extends in the vertical direction.

As soon as the beverage vessel is rotated around the horizontal axis, the lid remains in the horizontal position and opens the closure element such that the beverage can be poured out of the beverage vessel without any need of touching a surface that is in contact with the beverage in the beverage container.

In one embodiment the beverage vessel may comprise a stop means that is mounted to at least one of the rods at a position opposite to the lid and restricts the pivoting angle range of the lid.

In one embodiment the closure element further comprises a counter weight that is mounted to at least one of the rods at the position opposite to the lid. The counter weight supports the lid in keeping its essentially horizontal position to the environment of the beverage vessel, if the beverage vessel is rotated around the horizontal axis for pouring beverage out of the beverage container. The counter weight may act as a stop means.

The light emitter is positioned at the bottom of the beverage container and the light emitted by the light emitter may pass through the beverage before entering in the light distribution element. The light emitter may comprise a single light source, such as LED, a laser diode or the like. The light emitter may comprise a plurality of light sources, wherein the light sources emit light with different colors (wavelength).

The closure element of the beverage vessel may further comprise a light conducting section. The light conducting section may be formed by a hollow portion extending particularly in the grip element.

The beverage vessel may further comprise a rechargeable battery and a controller located below the beverage container.

The beverage vessel may be a carafe or the like.

The beverage vessel may comprise a first temperature sensor adapted to measure the temperature of the beverage in the beverage container. The first temperature sensor may be arranged at the bottom of the beverage container. The beverage vessel may further comprise a fill level sensor adapted to measure the fill level of the beverage in the beverage container. In one embodiment the fill level sensor may be a weight sensor that measures the weight of the beverage container and the beverage therein. In one embodiment the fill level sensor may be a capacitive sensor formed by a transparent layer around the beverage container. The beverage vessel may have a transmitter for transmitting information and a receiver for receiving information. The transmitter and the receiver may implement any near field communication protocol or any other protocol such as Bluetooth, Wi-Fi, RFID or the like.

The light emitter may be implemented by a light emitting diode, a laser diode or the like. The beverage vessel may also comprise a controller adapted to control the first temperature sensor, the fill level sensor, the transmitter, the receiver and/or the light emitter.

In one embodiment the controller may be adapted to determine the temperature of the beverage in the beverage container and to control the light emitter depending on the temperature of the beverage in the beverage container. Thereby, the user may be informed, if the temperature of the beverage in the beverage container exceeds a predetermined threshold.

In one embodiment the controller may determine the fill level of the beverage in the beverage container and to control the light emitter depending on the fill level of the beverage in the beverage container. Thereby, the user of the beverage vessel or a service staff, such as restaurants staff, hotel staff, nursing staff or the like, may be informed that the beverage vessel has to be refilled.

In one embodiment the controller may determine the time span, during which the beverage has been in the beverage container. The controller may control the light emitter depending on the time span during which the beverage is in the beverage container. Thereby, the user and/or a service staff are informed that the beverage in the beverage container has to be replaced.

The controller may also be adapted to receive information about the ingredients of the beverage in the beverage container and to control the light emitter depending on the ingredients of the beverage in the beverage container. The term "ingredients of the beverage" also includes the type of beverage. Thereby, the user and the service staff are informed which type of beverage is in the beverage vessel and the user can drink his preferred beverage and the service staff can refill of the beverage vessel with the appropriate beverage. The information about the ingredients of the beverage may be transmitted by a beverage dispenser.

The controller may be adapted to determine the temperature of the beverage in the beverage container and to output a signal depending on the temperature of the beverage in the beverage container. The outputted signal may be an audio signal output by a loudspeaker and/or a message transmitted by the transmitter. By the message transmitted by the transmitter service staff, such as restaurants staff, hotel staff, hospital staff or the like can be informed that the beverage in the beverage vessel has to be replaced.

In one embodiment the controller can determine the fill level of the beverage in the beverage container and can output a signal depending on the fill level of the beverage in the vessel. Also in this embodiment, the signal may be an audio signal and/or a message transmitted by the transmitter to an electronic device associated to service staff, such as restaurants staff, hotel staff, hospital staff, nursing staff or the like.

In one embodiment the controller may determine the time span during which the beverage has been in the beverage container, and output a signal depending on the time span, during which the beverage has been in the beverage container. Also in this embodiment the outputted signal may be an audio signal outputted by a loudspeaker and/or a message transmitted by the transmitter to an electronic device associated to service staff. Thereby, the service staff and/or the user can be informed that the beverage in the beverage container has to be replaced.

The controller may be adapted to determine the amount of beverage the user has drunken in a pre-defined time span and to control the light emitter depending on the amount of beverage the user has drunken in the predefined time span. Thereby, the user can be requested to drink beverage until the predefined amount of beverage has been drunken by the user. The controller can also be adapted to determine the amount of beverage the user has drunken in a predefined time span and to output a signal depending on the amount of beverage the user has drunken in a predefined time span. The outputted signal can be an audio signal outputted by a loudspeaker and/or a message transmitted by the transmitter. The message may be transmitted to an electronic device associated to the service staff mentioned before, particularly hospital staff or other nursing staff to enable the staff to monitor the hydration of a patient and prevent dehydration.

In one embodiment the controller may be adapted to transmit the message indicating the amount of beverage the user has drunken in a predefined time span after receipt of a message by the receiver. The received message may be a message received from an electronic device associated to service staff and/or nursing staff that monitors the water consumption of a patient.

The beverage vessel may comprise a first temperature sensor adapted to measure the temperature of the beverage in the beverage container. The first temperature sensor may be arranged at the bottom of the beverage container. The beverage vessel may further comprise a fill level sensor adapted to measure the fill level of the beverage in the beverage container. In one embodiment the fill level sensor may be a capacitive sensor formed by a transparent layer around the beverage container. The beverage vessel may have a transmitter for transmitting information and a receiver for receiving information. The transmitter and the receiver may implement any near field communication protocol or any other protocol such as RFID, Bluetooth, Wi-Fi or the like.

The light emitter may be implemented by a light emitting diode, a laser diode or the like. The beverage vessel may also comprise a controller adapted to control the first temperature sensor, the fill level sensor, the transmitter, the receiver and/or the light emitter.

In one embodiment the controller may be adapted to determine the temperature of the beverage in the beverage container and to control the light emitter depending on the temperature of the beverage in the beverage container. Thereby, the user may be informed, if the temperature of the beverage in the beverage container exceeds a predetermined threshold.

In one embodiment the controller may determine the fill level of the beverage in the beverage container and to control the light emitter depending on the fill level of the beverage in the beverage container. Thereby, the user of the beverage vessel or a service staff, such as restaurants staff, hotel staff, nursing staff or the like, may be informed that the beverage vessel has to be refilled.

In one embodiment the controller may determine the time span, during which the beverage has been in the beverage container. The controller may control the light emitter depending on the time span during which the beverage is in the beverage container. Thereby, the user and/or a service staff are informed that the beverage in the beverage container has to be replaced.

The controller may also be adapted to receive information about the ingredients of the beverage in the beverage container and to control the light emitter depending on the ingredients of the beverage in the beverage container. The term ingredients of the beverage also includes the type of beverage. Thereby, the user and the service staff are informed which type of beverage is in the beverage vessel and the user can drink his preferred beverage and the service staff can refill the beverage vessel with the appropriate beverage. The information about the ingredients of the beverage may be transmitted by a beverage dispenser.

The controller may be adapted to determine the temperature of the beverage in the beverage container and to output a signal depending on the temperature of the beverage in the beverage container. The outputted signal may be an audio signal outputted by a loudspeaker and/or a message transmitted by the transmitter. By the message transmitted by the transmitter service staff, such as restaurants staff, hotel staff, hospital staff or the like can be informed that the beverage in the beverage vessel has to be replaced.

In one embodiment the controller can determine the fill level of the beverage in the beverage container and can output a signal depending on the fill level of the beverage in the vessel. Also in this embodiment, the signal may be an audio signal and/or a message transmitted by the transmitter to an electronic device associated to service staff, such as restaurants staff, hotel staff, hospital staff, nursing staff or the like.

In one embodiment the controller may determine the time span during which the beverage has been in the beverage container, and output a signal depending on the time span, during which the beverage has been in the beverage container. Also in this embodiment the outputted signal may be an audio signal output by a loudspeaker and/or a message transmitted by the transmitter to an electronic device associated to service staff. Thereby, the service staff and/or the user can be informed that the beverage in the beverage container has to be replaced.

The controller may be adapted to determine the amount of beverage the user has drunken in a pre-defined time span and to control the light emitter depending on the amount of beverage the user has drunken in the predefined time span. Thereby, the user can be requested to drink beverage until the predefined amount of beverage has been drunken by the user. The controller can also be adapted to determine the amount of beverage the user has drunken in a predefined time span and to output a signal depending on the amount of beverage the user has drunken in a predefined time span. The output signal can be an audio signal output by a loudspeaker and/or a message transmitted by the transmitter. The message may be transmitted to an electronic device associated to the service staff mentioned before, particularly hospital staff or other nursing staff to enable the staff to monitor the hydration of a patient and prevent dehydration.

In one embodiment the controller may be adapted to transmit the message indicating the amount of beverage the user has drunken in a predefined time span after receipt of a message by the receiver. The received message may be a message received from an electronic device associated to service staff and/or nursing staff that monitors the water consumption of a patient.

In one embodiment the beverage vessel may comprise a humidity sensor adapted to determine the humidity in the environment of the beverage vessel. Additionally or alternatively, the beverage vessel may comprise a second temperature sensor adapted to determine the temperature of the environment of the beverage vessel.

The vessel controller may be adapted to transmit by the transmitter of the portable beverage vessel a message representing at least one temperature value temperature value determined by the second temperature sensor. Additionally or alternatively, the vessel controller may be adapted to transmit by the transmitter of the portable beverage vessel a message representing at least one humidity value determined by the humidity sensor.

The invention also discloses a method of monitoring a beverage consumption and/or a consumption of minerals in the beverage of a user of a beverage vessel. The beverage vessel can be the beverage vessel disclosed above.

The method determines the physical activity of a user. The method determines the amount of beverage to be supplied to the user of the beverage vessel. Further, the method determines the type of minerals to be supplied to the user by the beverage vessel. The method also determines the amount of minerals to be supplied to the user of the beverage vessel. The method determines the amount of beverage, the type of minerals and the amount of minerals drunken by the user of the beverage vessel. Further, the method determines the amount of beverage to be drunken by the user of the beverage vessel based on the amount of beverage to be supplied to the user and the amount of beverage drunken by the user. The method may determine the type of minerals to be drunken by the user of the beverage vessel based on the type of minerals to be supplied to the user and the type of minerals drunken by the user. Further, the method determines the amount of minerals to be drunken by the user of the beverage vessel based on the amount of minerals to be supplied to the user and the amount of minerals drunken by the user. The method indicates to the user of the beverage vessel and the user of the user device the amount of beverage to be drunk.

Further, the method may indicate to the user of the beverage vessel and the user of the user device the type of minerals to be drunk. The method further indicates to the user of the beverage vessel and the user of the user device the amount of minerals to be drunk. Thereby, the method ensures that the user drinks the type of minerals and the amount of minerals that correspond to the physical activity of the user. It is to be understood that the method may also determine the amount and type of minerals that are consumed by the user by food and to adapt the type and/or the amount of minerals to be drunken by the user.

In one embodiment the steps of determining the physical activity of a user, the step of determining the amount of beverage to be supplied to the user of the beverage vessel, the step of determining the type of minerals to be supplied to the user of the beverage vessel and the step of determining the amount of minerals to be supplied to the user of the beverage vessel may be executed by a user device. A user device may be a personal electronic device, such as a smart phone, a smart watch, a tablet computer, a wearable computer or the like. In one embodiment the step of determining the amount of beverage, the type of minerals and the amount of minerals drunken by the user of the beverage vessel is executed by the beverage vessel. The smart beverage vessel can cooperate with software running on the personal device, such as an app.

The step of indicating to the user of the beverage vessel and/or the user of the user device the type of minerals to be drunken, and the step of indicating the amount of minerals to be drunken to the user of the beverage vessel and the user of the user device the amount of minerals to be drunken can be executed by a beverage dispenser adapted to fill the beverage vessel. In this embodiment the user can select on an input device of the beverage dispenser whether he agrees to drink the suggested type and amount of minerals. The beverage having the suggested type and amount of minerals can be automatically filled into the beverage vessel after the user has confirmed the suggestion displayed by the beverage dispenser.

In another embodiment the step of indicating to the user of the beverage vessel and/or the user of the user device the type of minerals to be drunken, and the step of indicating to the user of the beverage vessel and/or the user of the user device the amount of minerals to be drunken can be executed alternatively or additionally on the user device. The proposed selection of beverage having the proposed type and amount of minerals is displayed on the user device.

In another embodiment the step of indicating to the user of the beverage vessel and/or the user of the user device the type of minerals to be drunken, and the step of indicating to the user of the beverage vessel and/or the user of the user device the amount of minerals to be drunken can be executed by the beverage vessel. The proposed beverage having the proposed type of minerals and the proposed amount of minerals can be displayed on the display of the beverage vessel.

The method further comprises the steps of identifying the user, who intends to refill the beverage vessel with the beverage dispenser. The step of identifying the user may comprise the step of communicating between the beverage dispenser and the user device. Alternatively or additionally the step of identifying the user may comprise the step of communicating with the beverage dispenser and the beverage vessel.

The method may further comprise the step of proposing to the user the type of minerals and amount of minerals. The step of proposing to the user the type of minerals and amount of minerals may comprise the step of displaying on the beverage dispenser the proposed minerals and amount of minerals and/or displaying on the user device the proposed minerals and amount of minerals and/or displaying on the display of the beverage vessel the proposed minerals and amount of minerals.

The step of proposing to the user the type of minerals and the amount of minerals may include the step of displaying a symbol indicating the type of minerals and amount of minerals in the beverage. The symbols may comprise text or a graphical symbol relating to a type of mineral water that comprises the proposed type of mineral and amount of minerals.

The method may comprise the steps of monitoring the temperature of the air around the portable beverage vessel and estimating the temperature of the beverage in the beverage vessel based on the temperature of the air around the portable beverage vessel.

The method may comprise the steps of monitoring the temperature of the air around the portable beverage vessel and determining the demand of a user for beverage and/or minerals based on the temperature of the air around the portable beverage vessel.

The method may comprise the steps of monitoring the humidity of the air around the portable beverage vessel and determining the demand of a user for beverage and/or minerals based on the humidity of the air around the portable beverage vessel. In one embodiment the method may determine the demand of the user for beverage and/or for minerals based on combining the temperature of the air around the portable beverage vessel determined by the beverage vessel and/or the humidity of the air around the portable beverage vessel determined by the beverage vessel.

In one embodiment the method may transmit the temperature of the air around the portable beverage vessel and/or the humidity of the air around the portable beverage vessel to the beverage dispenser and/or monitoring unit. Based on the transmitted temperature of the air around the portable beverage vessel and/or humidity of the air around the portable beverage vessel, the beverage dispenser and/or the monitoring unit can determine the amount of beverage and/or amount and type of minerals the user has to drink.

The invention also discloses a beverage dispenser adapted to dispense a beverage into a beverage vessel. The beverage vessel may be the beverage vessel described above. The beverage dispenser comprises a communication device, a controller and a display device. The communication device is adapted to communicate with the beverage vessel and/or a user device associated to a user of the beverage vessel. The controller is adapted to receive and/or determine data about a type of mineral and an amount of minerals to be drunken by the user. The display device is adapted to display a proposed type of minerals and a proposed amount of minerals to the user. If the user confirms the proposed types of minerals and the proposed amount of minerals, the beverage vessel is filled with a beverage, such as mineral water, that comprises the proposed type of minerals and the proposed amount of minerals. The mineral water may be filtered demineralized water that has been remineralized by mineral solutions stored in a plurality of solution tanks. The water dispenser may transmit the types of minerals, amount of minerals and/or amount of the beverage filled into the beverage vessel to the user device and/or beverage vessel.

The beverage dispenser and its components may be configured to execute the method disclosed above.

The invention also discloses a set comprising the above dispenser described above.

The invention also discloses a computer program product that is adapted to execute the steps of the method disclosed above, if loaded into a computer comprising a processor and a memory.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

BRIEF DESCRIPTION OF THE FIGURES OF THE DRAWINGS

The present invention is now described in further detail with reference to the accompanying drawings showing preferred and non-limiting embodiments of the invention, wherein.

DETAILED DESCRIPTION OF THE INVENTION

Figure 1:
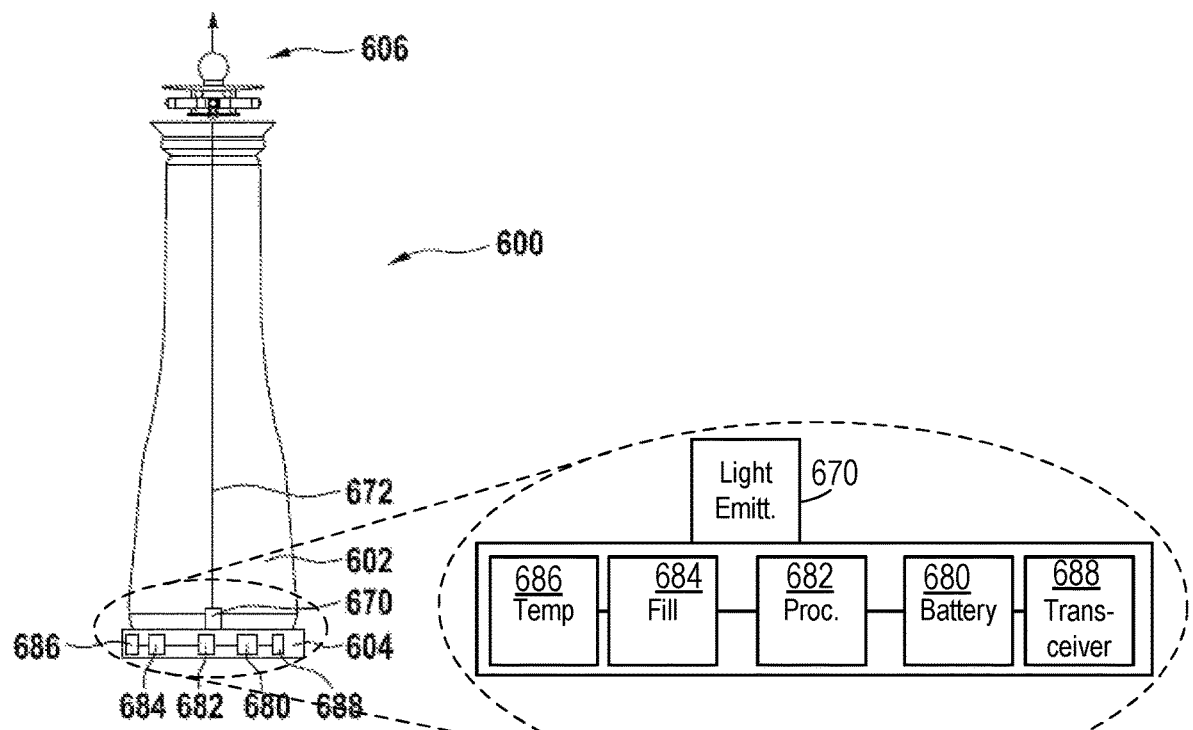
FIG. 1 shows a front view of a smart carafe.
Figure 2:
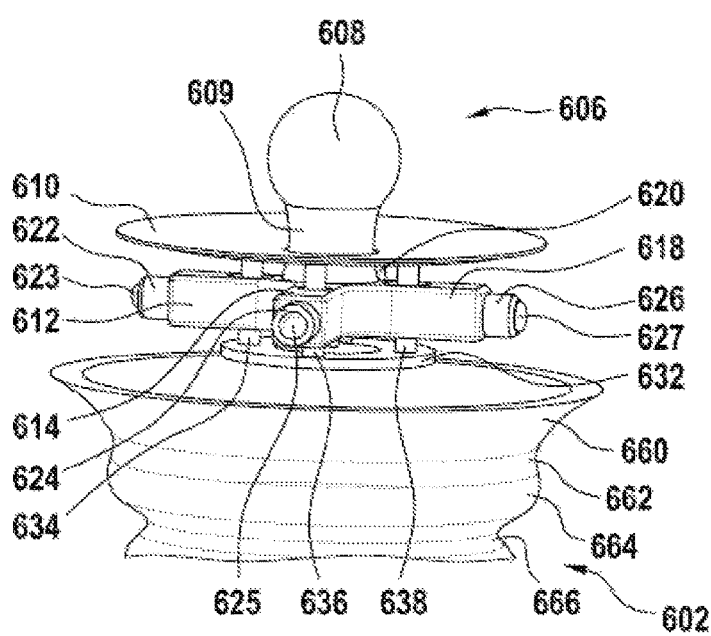
FIG. 2 shows a perspective view of the top of the smart carafe and a closure element.

A preferred embodiment of the invention is now described in detail. Referring to the drawings, like numbers indicate like parts throughout the views. Unless otherwise specifically indicated in the disclosure that follows, the drawings are not necessarily drawn to scale. The present disclosure should in no way be limited to the exemplary implementations and techniques illustrated in the drawings and described below. As used in the description herein and throughout the claims, the following terms take the meanings explicitly associated herein, unless the context clearly dictates otherwise: the meaning of "a," "an," and "the" includes plural reference, the meaning of "in" includes "in" and "on."

The smart carafe 600 shown in FIGS. 1 to 6 is an embodiment of the beverage vessel according to the present invention.

The smart carafe 600 according to the present invention comprises a beverage container 602, a closure element 606 and an optional controller 604.

Figure 3:
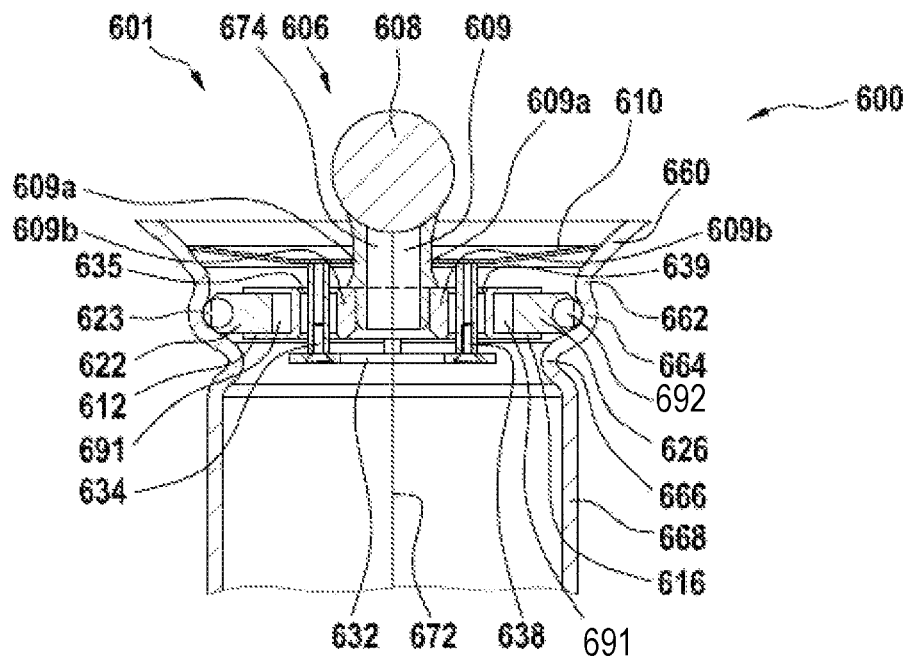
FIG. 3 shows a sectional view of the smart carafe and the closure element.
Figure 4:
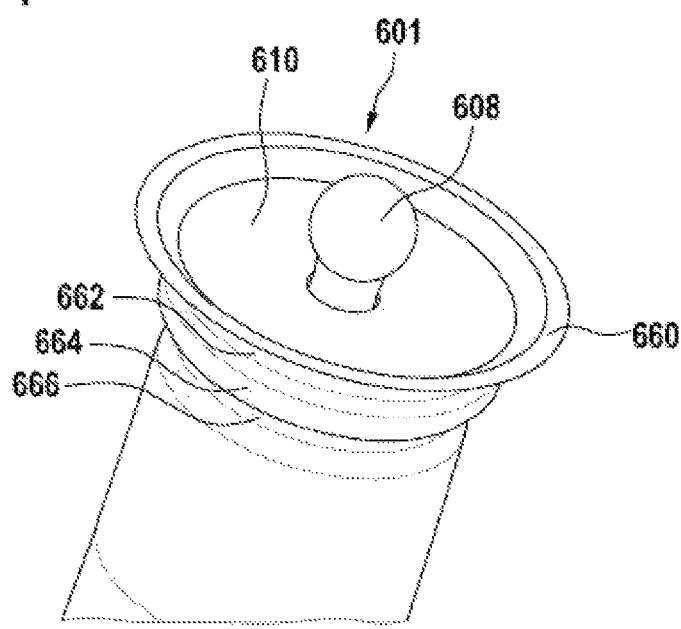
FIG. 4 shows a top view of the smart carafe and the closure element.
Figure 5:
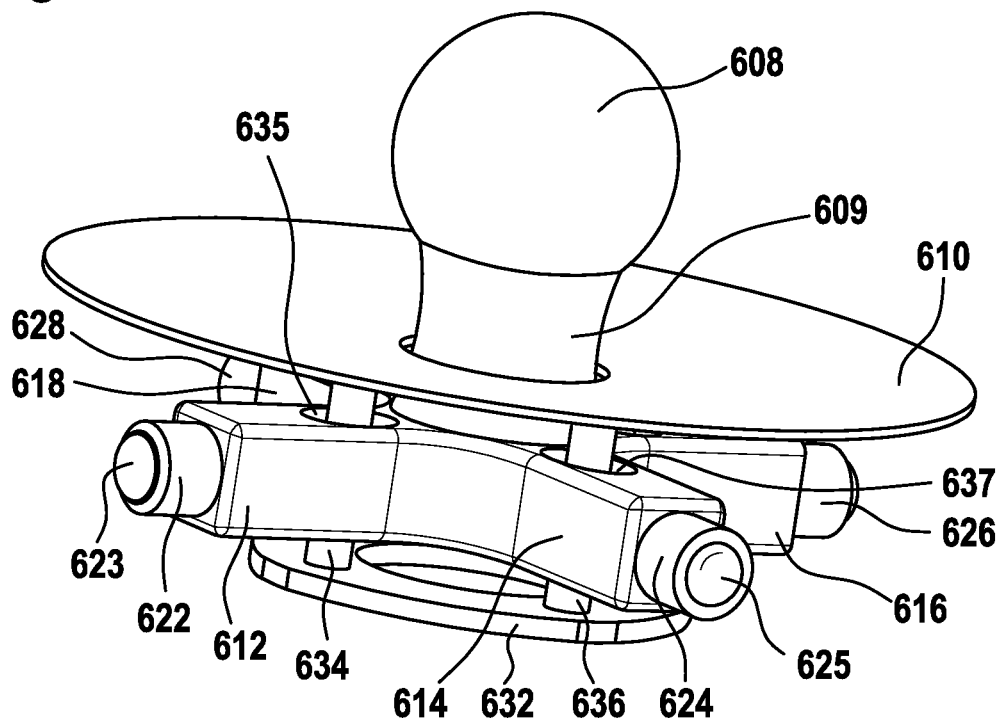
FIGS. 5 and 6 show prospective views of the closure element.
Figure 6:
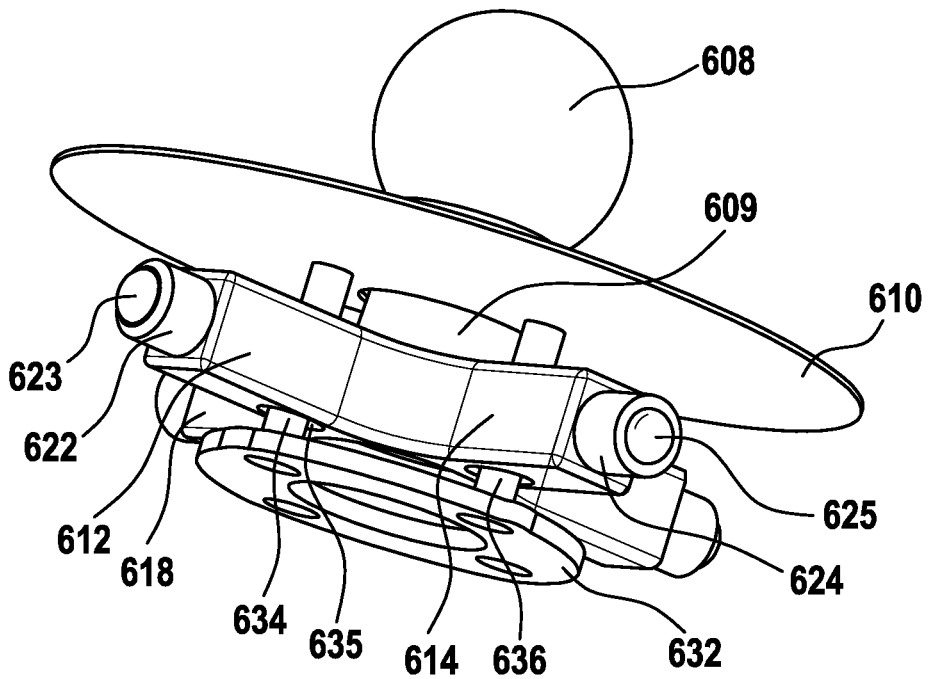

With reference to FIG. 3 the shape of the upper portion of the beverage container is explained. The beverage container comprises an upper opening 601, in which the closure element 606 can be releasably positioned. The beverage container 602 comprises a concave portion 664 forming a recess directed to the longitudinal axis of the beverage container 602 and smart carafe 600, respectively. The concave portion 664 may extend in circumferential direction around the beverage container 602. The concave portion 664 also forms a protuberance extending around the exterior surface of the beverage container 602. The protuberance of the outer surface of the vessel container 602 formed by the concave portion 664 extends away from the longitudinal axis of the beverage container 602 and smart carafe 600, respectively.

The beverage container 600 comprises an outward tapered portion at the opening 601. Below the outward tapered portion 660 a first convex portion 662 is arranged extending further inward in the direction of the longitudinal axis of the beverage vessel as the neighboring concave portion 664. Below the concave portion 664 a second convex portion 666 is arranged, wherein the second convex portion 666 extends further in the direction of the longitudinal axis of the beverage vessel as the first convex portion 662.

With reference to FIGS. 1 to 6 and particularly with reference to FIGS. 2, 3, 5 and 6 details of the closure element 606 are described. The closure element comprises a locking mechanism having four locking arm 612, 614, 616 and 618. In each locking arm 612, 614, 616, 618 a contact element 622, 624, 626, 628 is located. The contact element 622, 624, 626, 628 can move in the radial direction of the beverage container 602 within the respective locking arms 612, 614, 616, 618, in which the contact element is located. In one embodiment the contact element 622, 624, 626, 628 is partially accommodated by the respective locking arm 612, 614, 606, 618. Essentially each locking arm 612, 614, 616, 618 may comprise a recess in which the respective contact element 622, 624, 626, 628 is located. Within the recess an elastic element 691, 692, such as a spring may be located pressing the contact element 622, 626 in the radial outward direction.

Particularly, when the closure element 606 is positioned in the beverage container as is shown in FIG. 3, the contact elements 622, 626 are guided by a recess in the locking arms 612, 616 and biased by the elastic elements in the radially outward direction, such that the radially outward portion of the contact elements 622, 626 engages in the concave portion 664 of the beverage container 602. Thereby, the closure element 606 is held firmly by the concave portion 664 and the contact element.

At the radially outer portion of the contact elements 622, 624, 626, 628 a sphere 623, 625, 627 is arranged. The sphere 623, 625, 627 may be rotatably accommodated within the contact element 612, 614, 616, 618.

FIG. 3 shows the closure element 606 and the locking mechanism formed by the locking arms 612, 614, 616, 618 in its locked position. The closure element 606 further comprises an actuation element 609 forming also a grip element. A user can touch the actuation element 609 in order to move the closure element 606 into the opening 601 of the beverage container or to remove the closure element 606 from the opening 601 of the beverage container 606.

For removing the closure element 606 from the opening 601 of the beverage container 602, the user has to shift the actuation element 609 vertically upward. At the actuation element 609 first profile elements 609a are arranged. The first profile elements 609a engage with second profile elements 609b that are connected with the elastic elements and biasing the contact elements 622 and 626 into the locked position shown in FIG. 3. As soon as the user moves the actuation element 609 in the vertically upward direction, the first profile element 609a and the second profile element 609b disengage. Consequently, the second profile element 609b is moved in the radially inward direction and consequently the elastic elements are moved radially inward. Hence, also the contact elements 622 and 626 including the spheres 623 and 627 are moved radially inward. Therefore, contact elements 622, 626 including the spheres 623, 627 disengage from the concave portion 664 and the user can remove the closure element 606 from the opening 601 of the beverage container 602.

The closure element 606 comprises a lid 610 closing the opening 601, when the closure element 606 is engaged with the concave portion 664 by the contact elements 622, 626. The lid 610 is held by rods 634, 636 and 638 extending from the lower surface of the lid. The rods 634, 636, 638 extend essentially in vertical direction from the lower surface of the lid 610.

The rods 634, 636, 638 extend through openings 635, 637, 639 in the locking arms 612, 614, 616, 618. In the embodiments shown in FIGS. 1 to 6 the openings 635, 637, 639 are formed as elongated holes or in an elliptical shape. On the first side of the rods 634, 636, 638 the lid 610 is arranged. On the second side of the rods 634, 636, 638 opposite to the first side an optional counter weight 632 is arranged. The counterweight 632 may act as a stop means 632 that is mounted to at least one of the rods 634, 636, 638 at a position opposite to the lid and restricts the pivoting angle range of the lid 610.

When the user rotates the smart carafe 600 around the horizontal axis, the lid 610 is held in a horizontal position, since the rods 634, 636, 638 are moveably arranged in the opening 635, 637, 639. The counter weight 632 additionally supports the horizontal position of the lid 610 independent of the angle of the smart carafe 600 relative to the horizontal axis.

With reference to FIGS. 1 and 3 a further aspect of the smart carafe 600 according to the present invention is explained. The controller 604 can output a signal to a light emitter 670. Consequently, the light emitter 670 outputs light rays 672 passing through beverage in the beverage container 602. The light rays 672 pass a hollow portion 674 in the actuation element 609. The light rays 672 impinge on a light distribution element 608 that may also act as a grip portion. The light emitter element 608 scatters the light rays 672 such that the impinging light rays are directed to the periphery of the smart carafe 600 and visible for a user. The light distributor element may have opaque optical properties, scattering optical properties and/or diffracting optical properties for distributing the light around the smart carafe 600.

The light emitter 670 may be the light emitting diode (LED), a laser diode or the like. The light emitter may transmit light in a single color or may emit light in a plurality of different colors e. g. by a plurality of light emitters. The light emitter may transmit continuous light, flashing light or light periodically changing color for transmitting information.

The controller 604 may comprise a rechargeable battery 680, a processor 682, a fill level sensor 684 and a first temperature sensor 686. The fill level sensor 684 can be a weight sensor determining the weight of the beverage container 602 and the beverage therein. The first temperature sensor 686 can determine the temperature of the beverage in the beverage vessel 602. The processor 682 is coupled with the fill level sensor 684, the first temperature sensor 686 and the light emitter 670.

Figure 7:
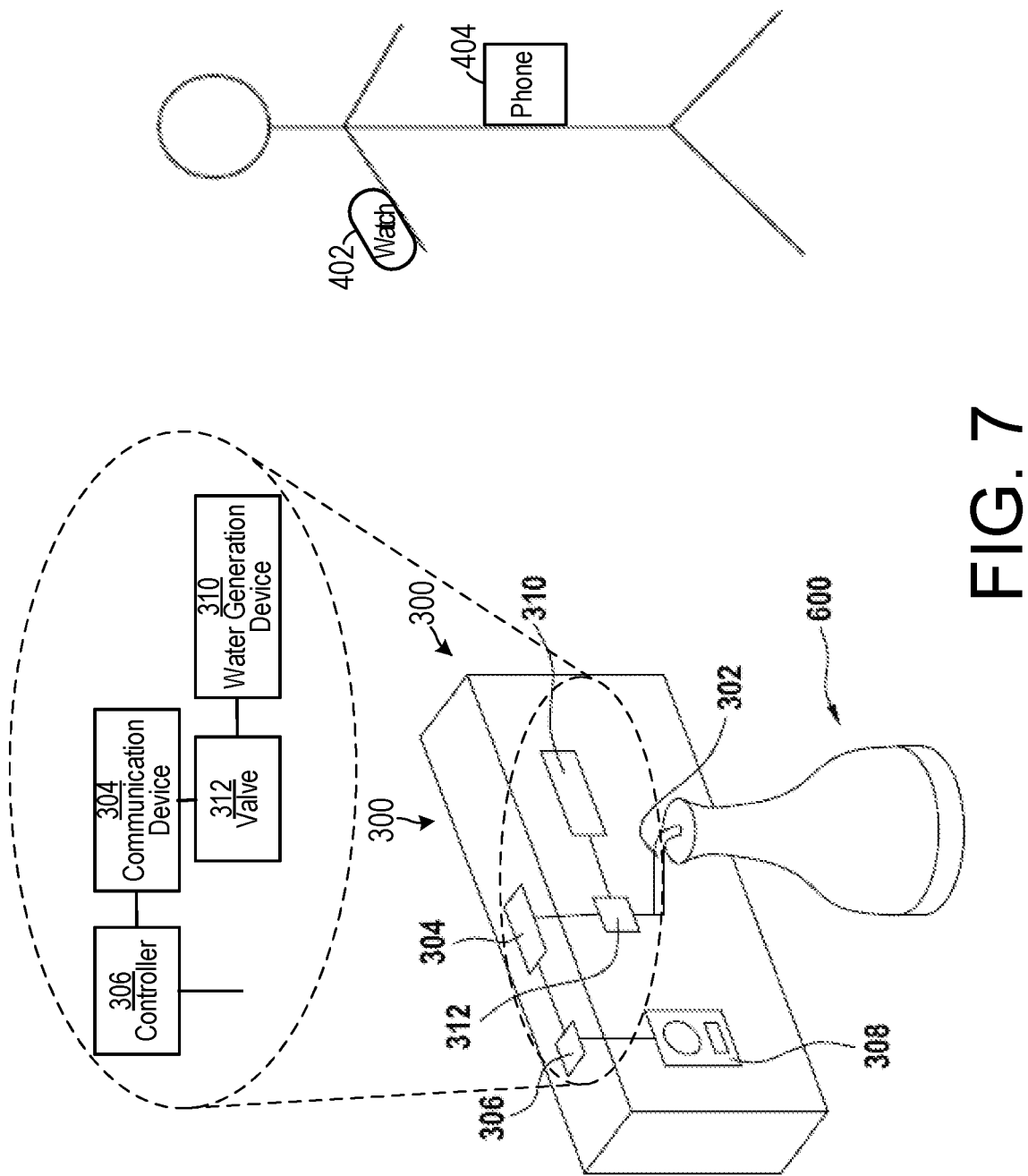
FIG. 7 shows the operation of the smart carafe with a water dispenser.

Reference is now made to FIG. 7 showing the operation of the beverage vessel (smart carafe) according to the present invention and a water dispenser 300 according to the present invention. The water dispenser 300 of the present invention comprises a communication device 304, a controller 306 and a display device 308. The controller 306 controls the display device 308, the communication device 304, a water generation device 310 and a valve 312. The water generation device 310 may mineralized prefiltered water or may be connected to a plurality of tanks in which different mineral waters are stored. The valve 312 is adapted to dispense a beverage via the tap 302 into the beverage vessel 600.

A user device 404, such as a smart phone, is associated to a user 400 and carried by the user. The smart phone 404 is coupled with a smart watch 402. The smart phone 404 and/or the smart watch 402 monitor the physical activity of the user, such as the number of steps. Further, the smart phone 404 and/or the smart watch 402 can monitor the heart frequency. Based on the physical activity a software (app) running on the smart phone 404 and/or on the smart watch 402 can calculate the amount of fluid, type of minerals and/or amount of minerals that have to be supplied to the user 400. The user may also enter food consumed into the software running on the smart phone 404 such that software can calculate the amount of beverage, minerals and/or type of minerals that have to be supplied to the user also based on the food consumed.

The fill level sensor 684 can determine how much beverage the user 400 has drunken. The water dispenser 300 can transmit to the controller 682 and/or to the user device 404 the type of minerals and amount of minerals dispensed by the water dispenser 300 into the smart beverage vessel. The controller 682 can transmit the amount of drunken beverage, type of drunken minerals and amount of minerals to the user device 404 and/or beverage dispenser 300 by the transceiver 688.

Accordingly, the software running on the mobile phone 404 can calculate the amount of beverage and/or type of minerals and/or amount of minerals that have to be drunken by the user 400. Such calculation can be based on the amount of beverage, type of minerals and/or amount of minerals that have to be supplied to the user 400 as well as the amount of beverage, type of minerals and/or amount of minerals that have been consumed by the user 400 from the beverage vessel 600 as well as the amount of liquid, type of minerals and/or amount of minerals that have been eaten by the user 400 as entered by the user 400 into the software running on the mobile phone 404. The beverage dispenser 300 transmits the types of minerals and the amounts of minerals in the beverage filled into the beverage vessel to the transceiver 688 of the beverage vessel 600 and the controller 682 of the beverage vessel 600 stores values of the types of minerals and the amounts of minerals in a memory. Thereby, the controller 682 of the beverage vessel 600 can determine the types and amounts of minerals drunken by the user based on the amount of beverage drunken by the user as determined by a fill level sensor 684.

The software running on the mobile phone 404 and/or the controller 306 of the beverage dispenser may calculate the amount of beverage, type of minerals and/or amount of minerals that have to be drunken by the user. The controller 306 of the water dispenser 300 may indicate a recommended beverage, such as a recommended type of mineral water on the display 308 of the beverage dispenser. The recommended mineral water may comprise the type of minerals and the amount of minerals that correspond as far as possible to the recommended type of minerals and/or amount of minerals to be drunken by the user. The user can confirm on the touch sensitive display 308 the proposed type of mineral water and thereafter, the controller 306 controls the water generation unit 310 and the valve 312 such that the recommended mineral water is supplied via the tap into the beverage vessel 600.

It is to be understood that the beverage dispenser can cooperate with a plurality of users 400 and beverage vessels 600. The controller 306 may have means for identifying a user 400 by its mobile phone 404 and/or by its beverage vessel 600. For identifying the mobile phone 404 and/or the beverage vessel 600, a wireless communication protocol such as RFID, Bluetooth, Wi Fi or the like may be used.

The beverage vessel 400 may also monitor the quality of the beverage in the beverage container 602 by the first temperature sensor 686. The temperature of the water may be measured by the first temperature sensor 686. Further, the controller 682 may determine the time span during which the water has been in the beverage vessel 102. If the temperature and/or the time span during which the water is in the beverage vessel exceeds a predetermined time span, a warning for a user is generated, such as by a message displayed on the mobile phone 404 and/or on the smart watch 402 and/or on the display 114 of the beverage vessel.

The inventive method may also determine, whether the user of the beverage vessel 600 has to drink liquid, such as water. The inventive method may display a message on the smart phone 404, the smart watch 402 and/or the beverage vessel 600, if the inventive method determines that the user has to drink additional liquid. The inventive method may also determine based on the physical activity of the user 400 that the user 400 has to drink additional minerals. If the inventive method determines that the user has to drink additional minerals, a message and/or light signal may be displayed by the mobile phone, the smart watch 402 and/or the smart beverage vessel 600. The message may also include the recommended type of minerals, amount of minerals and/or the recommended beverage, such as the recommended type of mineral water.

It is an advantage of the present invention that quality of a beverage in a beverage vessel may be monitored. Further, a user can be provided with tailored beverages comprising the type of minerals and amount of minerals that are actually needed by the body of the user.

Figure 8:
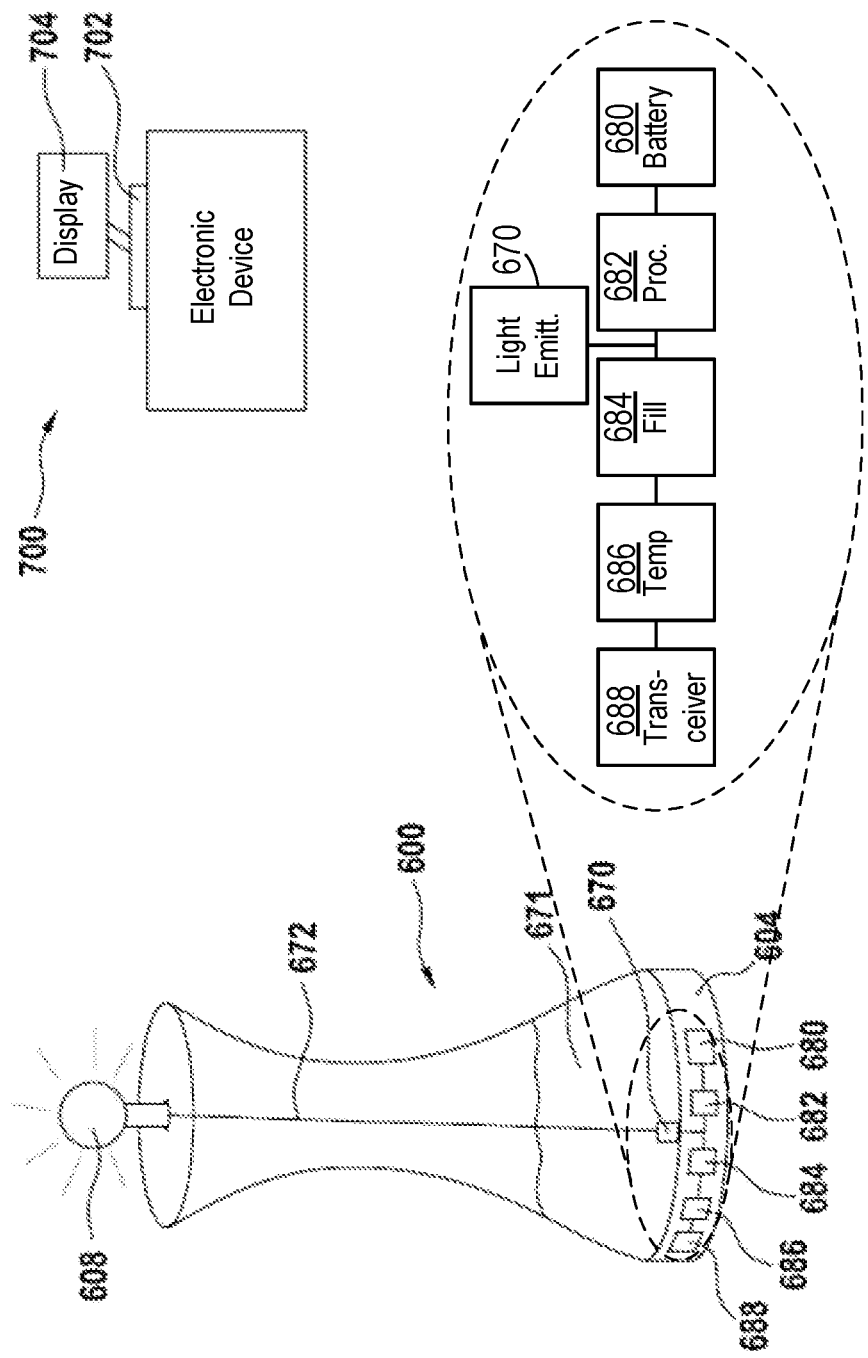
FIG. 8 shows a further operation scenario of the inventive smart carafe.

With reference to FIG. 8 operation of the inventive beverage vessel 600 is described. If the controller 682 determines by using the first temperature sensor 686 that the temperature of the beverage 671 exceeds a predetermined threshold, an audio signal can be outputted by the loudspeaker. Alternatively or additionally, the controller 682 may activate the light emitter 670 to emit light that passes through the beverage 671, the interior of the beverage container 602 and the light guide 686 to the partial sphere 608 of the actuation element 609. Alternatively or additionally the controller 682 may transmit a message by a transceiver 688 to an electronic device 702 associated to service staff, such as hotel staff, restaurants staff, hospital staff, nursing staff or the like in a service room 700. The message may be displayed on the display to 704 connected to the electronic device.

As soon as the partial sphere 608 emits light, or a message is displayed by the electronic device 602, the service staff is notified that the water in the beverage vessel 600 has to be substituted.

In one embodiment the controller 682 may monitor the fill level of the beverage 671 the beverage vessel 600. If the fill level of the beverage 671 is lower than a predetermined threshold, the controller may output an audio signal by the loudspeaker. Alternatively or additionally the controller 682 can output an optical signal by the light emitter 670, which passes through the beverage 671, the interior of the beverage container 602, the light guide 686 to the partial sphere 608 of the actuating element 609. Alternatively or additionally the controller can transmit a message by the transceiver 688 to the electronic device associated to the service staff mentioned before. By the light emitted by the partial sphere 608 and/or the message received by the electronic device 602, the service staff is informed that the beverage in the beverage vessel 600 has to be replaced.

In another embodiment the controller 682 may be adapted to emit light 670 depending on the type of beverage and/or the type and/or the amount of minerals in water, such as mineral water, remineralized water or the like. The light emitter 670 may comprise a plurality of light emitting diodes or laser diodes each having a different color. The color of the light emitted by the light emitter may change depending on the signal to be displayed, such as temperature of the beverage 671, fill level of the beverage 671, the type of beverage 671 and/or the time span, during which the beverage was in the beverage vessel 600. The type of beverage 671 and/or the type of minerals and/or the amount of minerals that has been filled into the beverage vessel 600 is transmitted by the beverage dispenser 400 via the transceiver 688 to the controller 682 and stored in a memory.

The controller 682 may be requested by the electronic device 602 associated to a service staff to transmit data about the beverage consumption of the user of the beverage vessel 600. The controller 682 may transmit in response to such request or based on another event, such as lapse of a predetermined time span, the amount of beverage, the user had been drinking from the beverage vessel 600 to the electronic device 602 using the transceiver 688. The controller 682 is also adapted to transmit light by the transceiver 670 to be displayed on the partial sphere 608, if the user has to drink additional amount of liquid.

All components of the closure element 606 may be produced by steel such as stainless steel. The beverage container 602 may be produced from glass. Both stainless steel and glass are chemical inert materials. Thereby, germ formation can be suppressed.

It is an advantage of the present invention that information may be displayed by beverage vessel in a manner that does not jeopardize the design of the beverage vessel. Further, the closure element is designed such that touching the closure element at surfaces that are in contact with beverage by the user may be avoided.

Although specific advantages have been enumerated above, various embodiments may include some, none, or all of the enumerated advantages. Other technical advantages may become readily apparent to one of ordinary skill in the art after review of the following figures and description. It is understood that, although exemplary embodiments are illustrated in the figures and described below, the principles of the present disclosure may be implemented using any number of techniques, whether currently known or not. Modifications, additions, or omissions may be made to the systems, apparatuses, and methods described herein without departing from the scope of the invention. The components of the systems and apparatuses may be integrated or separated. The operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. It is intended that the claims and claim elements recited below do not invoke 35 U.S.C. 112(f) unless the words "means for" or "step for" are explicitly used in the particular claim. The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A beverage vessel, comprising:
   a beverage container in which a beverage may be stored, wherein the beverage container has an upper opening through which beverage may be poured in and poured out of the beverage container and a wall extending from the upper opening to the bottom of the beverage container;
   a closure element adapted to be positioned in the upper opening of the beverage container;

a light distribution element arranged at the closure element;

a light emitter positioned such that the light emitted by the light emitter passes at least a part of the volume of the beverage container before entering the light distribution element; and a locking mechanism releasably locking the closure element at the beverage vessel;

wherein the light distribution element is adapted to distribute the light entering for the light emitter in the periphery of the beverage vessel;

wherein the closure element comprises an actuation element moveably mounted on the closure element, wherein the actuation element can be moved in a first position in which the locking mechanism is released and in a second position in which the locking mechanism is not released; and wherein the light distribution element is arranged on the actuation element.

2. The beverage vessel according to claim 1, wherein the beverage container comprises a concave portion in the wall and wherein the concave portion extends in the circumferential direction along the wall of the beverage container.

3. The beverage vessel according to claim 1, wherein:

the closure element comprises a grip element extending from the closure element in the vertical direction of the beverage vessel; and the light distribution element is arranged at the grip element.

4. The beverage vessel according to claim 3, further comprising a lid, positioned under the grip element and above the locking mechanism, wherein the lid is movably mounted to the locking mechanism.

5. The beverage vessel according to claim 4, wherein the lid is pivotally mounted to the locking mechanism.

6. The beverage vessel according to claim 1, wherein the light distribution element comprises at least a partial sphere.

7. The beverage vessel according to claim 1, wherein the light emitter is positioned at the bottom of the beverage container.

8. The beverage vessel according to claim 1, wherein the closure element further comprises a light conducting section that can be formed by at least one of the following:

a hollow portion extending vertically in the grip element; and a light guide extending vertically in the grip element.

9. The beverage vessel according to claim 1, wherein a rechargeable battery and controller are arranged below the beverage container.

10. The beverage vessel according to claim 1, further comprising at least one of the following:

a first temperature sensor adapted to measure the temperature of the beverage in the beverage container;

a fill level sensor adapted to measure the fill level of the beverage in the beverage container;

a weight sensor arranged under the bottom of the beverage container and adapted to measure the weight of the beverage container and the beverage therein;

a transmitter for transmitting information;

a receiver for receiving information;

a LED forming the light emitter;

a laser diode forming the light emitter.

11. The beverage vessel according to claim 1, wherein the beverage vessel further comprises:

a controller;

a first temperature sensor; a fill level sensor;

a transmitter;

a receiver; and a light emitter, and wherein the controller is adapted to do at least one of the following:

control at least one of the first temperature sensor, the fill level sensor, the transmitter, the receiver and the light emitter;

determine the temperature of the beverage in the beverage container and to control the light emitter depending on the temperature of the beverage in the beverage container;

determine the fill level of the beverage in the beverage container and to control the light emitter depending on the fill level of the beverage in the beverage container;

determine a time span, during which the beverage has been in the beverage container, and to control the light emitter depending on the time span, during which the beverage is in the beverage container; and receive information about the ingredients of the beverage in the beverage container and to control the light emitter depending on the ingredients of the beverage in the beverage container.

12. The beverage vessel according to claim 11, wherein the controller is adapted to do at least one of the following:

determine a temperature of the beverage in the beverage container and to output a signal depending on the temperature of the beverage in the beverage container;

determine a fill level of the beverage in the beverage container and to output a signal depending on the fill level of the beverage in the beverage container; and determine a time span, during which the beverage has been in the beverage container, and to output a signal depending on the time span, during which the beverage has been in the beverage container.

13. The beverage vessel according to claim 12, further comprising at least one of the following:

a humidity sensor adapted to determine the humidity in the environment of the beverage vessel; and a second temperature sensor adapted to determine the temperature of the environment of the beverage vessel.

14. The portable beverage vessel according to claim 12, wherein the controller is adapted to at least one of the following:

to transmit by the transmitter of the beverage vessel a message representing at least one temperature value determined by the second temperature sensor; and to transmit by the transmitter of the beverage vessel a message representing at least one humidity value determined by the humidity sensor.

* * * * *